(12) United States Patent
Kadkly et al.

(10) Patent No.: US 7,385,688 B1
(45) Date of Patent: Jun. 10, 2008

(54) MULTI-SPOT ILLUMINATION AND COLLECTION OPTICS FOR HIGHLY TILTED WAFER PLANES

(75) Inventors: Azmi Kadkly, Cupertino, CA (US); Mehdi Vaez-Iravani, Los Gatos, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 387 days.

(21) Appl. No.: 11/158,441

(22) Filed: Jun. 22, 2005

(51) Int. Cl.
*G01N 21/00* (2006.01)
(52) U.S. Cl. .................. 356/237.5; 356/237.4
(58) Field of Classification Search .. 356/237.1–237.6, 356/239.3–239.8, 445–448, 394
See application file for complete search history.

(56) References Cited

U.S. PATENT DOCUMENTS

| | | | |
|---|---|---|---|
| 5,024,529 A | 6/1991 | Svetkoff et al. | |
| 5,151,888 A | 9/1992 | Shikichi et al. | |
| 5,576,831 A | 11/1996 | Nikoonahad et al. | |
| 5,767,962 A | 6/1998 | Suzuki et al. | |
| 6,208,411 B1 | 3/2001 | Vaez-Iravani | |
| 6,578,961 B2* | 6/2003 | Vaez-Iravani | 356/237.2 |
| 7,068,363 B2 | 6/2006 | Bevis et al. | |
| 2005/0110987 A1* | 5/2005 | Furman et al. | 356/237.4 |

OTHER PUBLICATIONS

U.S. Appl. No. 11/158,440, filed Jun. 22, 2005, Kadkly et al.

* cited by examiner

*Primary Examiner*—Gregory J. Toatley, Jr.
*Assistant Examiner*—Tri Ton
(74) *Attorney, Agent, or Firm*—Baker & McKenzie LLP

(57) ABSTRACT

Multi-spot illumination and collection optics for highly tilted wafer planes are provided. One system configured to provide illumination of a wafer for inspection includes one or more optical elements configured to direct light to an entrance pupil. The system also includes a diffractive optical element positioned at the entrance pupil and configured to separate the light into individual beams. In addition, the system includes a set of optical elements configured to focus the individual beams to a wafer plane to form spatially separated spots on the wafer plane. The wafer plane is arranged at an oblique angle to the entrance pupil.

19 Claims, 7 Drawing Sheets

MULTI-SPOT ILLUMINATION AND COLLECTION OPTICS FOR HIGHLY TILTED WAFER PLANES

BACKGROUND OF THE INVENTION

1. Field of the Invention

This invention generally relates to multi-spot illumination and collection optics for highly tilted wafer planes. Certain embodiments relate to a system configured to provide illumination of a wafer for inspection. Other embodiments relate to a system configured to collect and detect light scattered from a wafer.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semiconductor devices. Accordingly, much work has been done in the field of wafer inspection to increase the sensitivity of inspection systems to smaller and smaller defects.

Another concern that becomes more prevalent for inspection system manufacturers and customers alike as defect sizes decrease is the difficulty of detecting relatively small defects on relatively rough wafer surfaces. In particular, previously, the scattering of light from relatively rough surfaces did not substantially limit inspection system performance since the defects being detected were relatively large. However, as the size of defects decreases, the amount of light scattered from the defects may also decrease. As such, the amount of light scattered from defects of relatively small size may be much closer to the amount of light scattered from relatively rough surfaces thereby reducing the sensitivity of many systems for inspection of such surfaces. Therefore, although many currently available inspection systems are capable of detecting relatively large defects on relatively rough surfaces and/or relatively small defects on relatively smooth surfaces, there is still a need for an inspection system that can detect relatively small defects on relatively rough surfaces.

One example of a wafer inspection system configuration that is suitable for detecting relatively large defects such as contamination on relatively rough surfaces is a "double-dark field" configuration. Such a configuration uses S-polarized (i.e., polarized perpendicular to the plane of incidence) obliquely incident light that results in a dark fringe at the surface, which produces substantially little light scattered from the surface itself. Such illumination used with an analyzer oriented perpendicular to the plane of scatter (i.e., for detection of S-polarized light) and an aperture limited to "side-angle collection" (e.g., limiting the collected light to azimuthal angles reasonably close to +/−90 degrees with respect to the plane of incidence) can reduce the contribution of unwanted surface scattering to the background noise by a large amount. Large particles and defects located on the surface of the wafer can be detected relatively easily using this configuration since they are less affected by the dark fringe effect and therefore perturb (or scatter) the incident electric field efficiently compared to the surface.

This configuration performs well for defects having a size greater than approximately one-half the wavelength of the incident light. Such defect detection capability is achievable since the S-S side-angle configuration is substantially effective at reducing the scattering from the surface as described above. Unfortunately, this configuration is also effective at reducing the scattering from relatively small defects (e.g., defects having a size that is smaller than one-half the wavelength of the incident light). Therefore, using a typical illumination wavelength of about 488 nm, such a configuration can detect defects having sizes of about 250 nm and larger. For particles below this size, the signal level decreases rapidly. Such inspection capability previously met the needs of semiconductor manufacturers since semiconductor processes using materials that have rough surfaces were susceptible to failure caused by defects having such defect sizes. However, today customers are expressing the need to detect defects having a size of 150 nm, 100 nm, or even smaller, on wafers having relatively rough surfaces. Therefore, even an ultraviolet (UV) wavelength of, say, 355 nm in this configuration may not be sufficient for detecting defects of such small sizes on wafers having a relatively rough upper surface.

Many inspection systems such as those described above are configured to image a single spot or line on the wafer plane at normal and/or oblique angles of incidence using spherical and/or cylindrical lenses. The single spot or line imaging of these systems also contributes, at least in part, to the relatively low sensitivity (e.g., relatively low signal-to-noise ratio, SNR) of the systems for inspection of rough surfaces. In particular, since a single spot or line on the wafer plane is relatively large (particularly in comparison to the size of the defects typically being detected), the light scattered from the illuminated spot or line will contain a relatively large amount of scattering from the surface of the wafer. Such scattering may be relatively low for relatively smooth surfaces. However, the scattered light from relatively rough wafer surfaces may be much higher and will, therefore, adversely affect the sensitivity of the inspection system.

Obviously, therefore, one way to increase the SNR for relatively rough surface inspection is to decrease the size of the spot on the wafer. However, decreasing the size of the optical spot on the wafer will decrease the throughput of the inspection system, and the single spot scanning based systems already have relatively slow scanning rates. As such, attempts have been made to image multiple smaller spots on a wafer plane such that a larger area of the wafer plane can be illuminated simultaneously by the multiple spots thereby maintaining the throughput of the inspection system without causing relatively large amounts of scattering from the surface of the wafer.

Systems have been developed that can image multiple spots onto a wafer plane at a normal angle of incidence. However, systems for imaging multiple spots on tilted wafer planes (e.g., a wafer plane arranged at an oblique angle with respect to an optical axis of the system) have not been achieved. The current lack of a solution for a multi-spot imaging system for tilted wafer planes may be attributed, at least in part, to the fact that systems for imaging multiple spots onto a wafer plane at a normal angle of incidence will not suffer from the dramatic defocus and astigmatism problems that must be overcome to provide multi-spot images at oblique angles of incidence. Therefore, systems that are configured to image multiple spots onto a wafer plane at a normal angle of incidence will have dramatically different optical configurations (and much simpler optical configurations) than systems that can image multiple spots onto a wafer plane at an oblique angle of incidence.

Furthermore, there is no currently available system that can be used for imaging light scattered from a multi-spot obliquely illuminated wafer at the level of performance required. In particular, currently used collection optics for single spot illumination and normal angle of incidence multi-spot illumination cannot be used effectively to image light scattered from a multi-spot obliquely illuminated wafer. For example, single spot collection systems are non-imaging systems and, therefore, cannot be used to image light from different spots on the wafer plane to different spatially separated positions in an image plane. In addition, the collection optics used for normal angle of incidence multi-spot systems is limited by a low numerical aperture (e.g., about 0.50) and low sensitivity, particularly with respect to relatively rough wafer surfaces.

Accordingly, it would be advantageous to develop systems and methods for illuminating a wafer with spatially separated spots formed on the wafer plane at an oblique angle of incidence and for collecting and detecting light scattered from such spots thereby providing relatively high sensitivity inspection capability, particularly in terms of absolute defect sensitivity and sensitivity for relatively rough surface inspection, while meeting, or even exceeding, throughput requirements.

SUMMARY OF THE INVENTION

The following description of various system and method embodiments is not to be construed in any way as limiting the subject matter of the appended claims.

One embodiment relates to a system configured to provide illumination of a wafer for inspection. The system includes one or more optical elements configured to direct light to an entrance pupil. The system also includes a diffractive optical element positioned at the entrance pupil. The diffractive optical element is configured to separate the light into individual beams. In addition, the system includes a set of optical elements configured to focus the individual beams to a wafer plane to form spatially separated spots on the wafer plane. The wafer plane is arranged at an oblique angle to the entrance pupil.

In one embodiment, the spots are diffraction limited. In another embodiment, each of the spots has a Gaussian profile. In an additional embodiment, each of the individual beams is substantially collimated. In some embodiments, an intensity of each of the spots is approximately equal. In a further embodiment, a size of each of the spots is approximately equal. The size of the spots may be selected such that a substantial amount of light scattered from the spots is not light scattered from a rough surface of the wafer. In additional embodiments, the oblique angle is about 70 degrees.

In another embodiment, the set of optical elements includes two optical elements. The two optical elements are decentered with respect to x and y axes of a plane of the entrance pupil. The two optical elements are also tilted with respect to the y axis. In one such embodiment, the set of optical elements also includes a third optical element. The third optical element is decentered with respect to the x and y axes of the plane of the entrance pupil. The third optical element is also tilted with respect to the x axis.

In a preferred embodiment, the set of optical elements is configured to correct asymmetric focus error in the spots. In another embodiment, the set of optical elements includes refractive optical elements. In a further embodiment, the set of optical elements includes one or more truncated optical elements.

In one embodiment, the diffractive optical element or the set of optical elements is rotated about a z axis of a plane of the entrance pupil. In another embodiment, the spots are located within an area of the wafer plane such that an entire lateral dimension of the area is illuminated by the spots as the spots are scanned across the wafer plane. Each of the embodiments of the system described above may be further configured as described herein.

Another embodiment relates to a system configured to inspect a wafer. The system includes one or more optical elements configured to direct light to an entrance pupil. The system also includes a diffractive optical element positioned at the entrance pupil. The diffractive optical element is configured to separate the light into individual beams. In addition, the system includes a set of optical elements configured to focus the individual beams to a wafer plane to form spatially separated spots on the wafer plane. The wafer plane is arranged at an oblique angle to the entrance pupil. The system further includes a detection subsystem configured to collect and detect light scattered from each of the spots. Signals generated by the detection subsystem in response to the detected light can be used to detect defects on the wafer. The detection subsystem may be further configured as described herein.

In one embodiment, the spots are diffraction limited. In another embodiment, a size of each of the spots is approximately equal. The size of the spots may be selected such that a substantial amount of the light scattered from each of the spots is not light scattered from a rough surface of the wafer. In a preferred embodiment, the set of optical elements is also configured to correct asymmetric focus error in the spots. In a further embodiment, the spots are located within an area of the wafer plane such that an entire lateral dimension of the area is illuminated by the spots as the spots are scanned across the wafer plane. Each of the embodiments of the system described above may be further configured as described herein.

An additional embodiment relates to a method for providing illumination of a wafer for inspection. The method includes directing light to an entrance pupil. The method also includes separating the light into individual beams at the entrance pupil. In addition, the method includes focusing the individual beams to a wafer plane to form spatially separated spots on the wafer plane. The wafer plane is arranged at an oblique angle to the entrance pupil. This method may also include any other step(s) described herein.

A further embodiment relates to a system configured to collect and detect light scattered from a wafer. The system includes a set of optical elements configured to collect light scattered from spatially separated spots formed on a wafer plane at an oblique angle of incidence. The set of optical elements is also configured to focus the light to corresponding spatially separated positions in an image plane. The system also includes a detection subsystem configured to separately detect the light focused to the spatially separated positions in the image plane.

In one embodiment, a numerical aperture of the set of optical elements is equal to 0.94. In another embodiment, a field size of the set of optical elements is equal to or larger than an area in which the spots formed on the wafer plane are located. In an additional embodiment, the set of optical elements includes three spherical/aspheric optical elements. In a further embodiment, the set of optical elements includes refractive optical elements. In some embodiments, the set of optical elements includes a first optical element, and a section of the first optical element is removed such that light can be directed through the section to the wafer plane at the oblique angle of incidence. In yet another embodiment, the set of optical elements is overcorrected to reduce degradation in imaging quality at the image plane due to focus error.

In one embodiment, the system includes a set of optical fibers configured to separately transmit the light from the spatially separated positions in the image plane to the detection subsystem. In one such embodiment, the set of optical fibers includes a linear array of optical fibers. In another such embodiment, a diameter of each of the optical fibers is about 250 microns. In some embodiments, a magnification ratio of the system is greater than about 30×.

In another embodiment, the detection subsystem includes individual detectors having positions that correspond to the spatially separated positions in the image plane. Each of the embodiments of the system described above may be further configured as described herein.

Another embodiment relates to a system configured to inspect a wafer. This system includes an illumination subsystem configured to direct light to a wafer plane at an oblique angle of incidence to form spatially separated spots on the wafer plane. The illumination subsystem may be further configured as described herein. The system also includes a set of optical elements configured to collect light scattered from the spots. The set of optical elements is also configured to focus the collected light to corresponding spatially separated positions in an image plane. In addition, the system includes a detection subsystem configured to separately detect the light focused to the spatially separated positions in the image plane. Signals generated by the detection subsystem in response to the detected light can be used to detect defects on the wafer.

In one embodiment, a numerical aperture of the set of optical elements is equal to 0.94. In another embodiment, a field size of the set of optical elements is equal to or larger than an area in which the spots on the wafer plane are located. In an additional embodiment, the set of optical elements includes a first optical element. A section of the first optical element may be removed. In such an embodiment, the illumination subsystem is configured to direct the light through the section to the wafer plane. In a further embodiment, the set of optical elements is overcorrected to reduce degradation in imaging quality at the image plane due to focus error.

In one embodiment, the system also includes a set of optical fibers configured to separately transmit the light from the spatially separated positions in the image plane to the detection subsystem. In another embodiment, the detection subsystem includes individual detectors having positions that correspond to the spatially separated positions in the image plane. Each of the embodiments of the system described above may be further configured as described herein.

An additional embodiment relates to a method for collecting and detecting light scattered from a wafer. This method includes collecting light scattered from spatially separated spots formed on a wafer plane at an oblique angle of incidence. The method also includes focusing the light to corresponding spatially separated positions in an image plane. In addition, the method includes separately detecting the light focused to the spatially separated positions in the image plane. This method may also include any other step(s) described herein.

BRIEF DESCRIPTION OF THE DRAWINGS

Other objects and advantages of the invention will become apparent upon reading the following detailed description and upon reference to the accompanying drawings in which.

Figure 1:
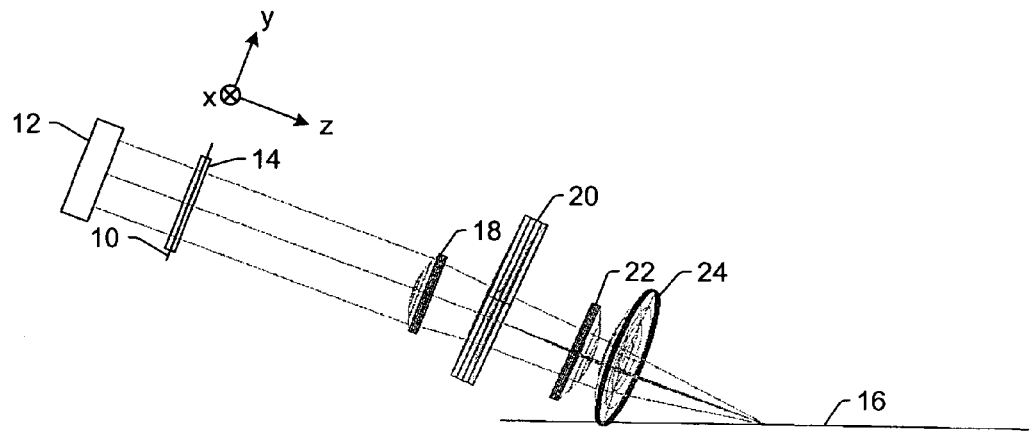
FIG. 1 is a schematic diagram illustrating a cross-sectional view of one embodiment of a system configured to provide illumination of a wafer for inspection.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "defect" generally refers to any abnormality or undesirable feature that may be formed on or within a wafer.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a system configured to provide illumination of a wafer for inspection. The system includes one or more optical elements configured to direct light to entrance pupil 10. The one or more optical elements include at least one light source (not shown). One example of an appropriate light source is a laser that is configured to emit light at an ultraviolet (UV) wavelength of about 355 nm. However, the light source may include any other appropriate light source known in the art. In addition, the one or more optical elements may include more than one light source (not shown). The light sources may be configured to emit light having different properties such as wavelength.

The one or more optical elements may also include optical element(s) (not shown) that are configured to alter the properties of the light directed to the entrance pupil. For example, the optical element(s) may include one or more polarizers, one or more filters, and beam shaping element(s). In addition, the one or more optical elements may include one or more light directing elements. For example, as shown in FIG. 1, the one or more optical components may include refractive element 12. Refractive element 12 may be, for example, a collimating lens or a beam expanding/collimating lens. The light directing elements may also or alternatively include reflective elements.

The system also includes diffractive optical element (DOE) 14 positioned at entrance pupil 10. DOE 14 may be positioned in the plane of entrance pupil 10. In addition, DOE 14 may be substantially centered with respect to the entrance pupil plane and rotated at a specified angle. DOE 14 is configured to separate the light directed to the entrance pupil into individual beams. The DOE may also be configured as a high efficiency DOE. In other words, the efficiency of the DOE may be from about 65% to about 75%. The DOE may be further configured to generate individual beams having approximately equal intensity. The substantially uniform intensity of the individual beams may be attributable to the relatively high efficiency of the DOE. If the light directed to the DOE is substantially collimated, each of the individual beams generated by the DOE is also substantially collimated.

The DOE is configured to separate the light into at least three individual beams. In one embodiment, the DOE may be configured to generate 19 substantially collimated individual beams of light. In general, a large number of individual beams may be desirable since the number of individual beams determines the number of spatially separated spots that can be formed on the wafer plane. However, when selecting the number of individual beams, it is important to take into consideration the fact that as the number of individual beams into which the light is separated increases, the complexity of the optical system also increases. In addition, the DOE may be a diffraction grating that is configured to generate a two-dimensional array of individual beams (instead of a one-dimensional array of individual beams as is usually the case) in which case the DOE may not be rotated with respect to the pupil's z-axis. Diffraction gratings configured to generate a two-dimensional array of individual beams are commercially available from, for example, Heptagon, Espoo, Finland.

The individual beams generated by the DOE are directed to a set of optical elements. The set of optical elements includes lenses that have both spherical and aspheric surfaces. The set of optical elements is located a distance away from the DOE. The set of optical elements is configured to focus the individual beams to wafer plane 16 to form spatially separated spots (not shown in FIG. 1) on wafer plane 16. As shown in FIG. 1, wafer plane 16 is arranged at an oblique angle to the entrance pupil. In one embodiment, the oblique angle may be about 70 degrees. However, the oblique angle may vary depending on, for example, the configuration of the illumination system, the configuration of an inspection system in which the illumination system is used, and/or characteristics of the wafer to be inspected.

Since the DOE is used to generate the individual beams that are focused to the wafer plane, each of the spots formed on the wafer plane may be diffraction limited. In this manner, the illumination system advantageously has diffraction limited performance. In addition, each of the spots may have a Gaussian profile. In particular, the spots may have Gaussian profiles if the light provided by the light source has a Gaussian profile. In other words, the intensity profiles of the spots formed on the wafer plane may vary depending on the intensity profile of the light directed to the entrance pupil.

Each of the spots formed on the wafer plane may also have an elliptical shape since the wafer plane is arranged at an oblique angle with respect to the entrance pupil. The elliptically shaped spots may have a major axis to minor axis ratio of about 3:1. The major axis to minor axis ratio is a function of the angle of incidence. Therefore, if the angle of incidence changes, the major axis to minor axis ratio of the spots formed on the wafer plane will also change.

In addition, the size of each of the spots may be approximately equal. Examples of appropriate sizes for the spots formed on the wafer plane include 3 microns×9 microns and 5 microns×15 microns. The size of the spots may vary depending on a number of parameters of the system such as the size of the limiting aperture, which determines the size of the light beam at the entrance pupil, and the configuration of the DOE. In addition, as the size of the spots formed on the wafer plane decreases, the complexity of the optical system may increase, for example, to further compensate for any aberrations that may be more pronounced for smaller spot sizes. If on the other hand the size of the illuminating beam is fixed, the spot size can still be changed by changing the effective focal length (EFL) of the optical system. The spot size can further be changed by changing the wavelength of the illuminating light source. In general and for a rotationally symmetric system, the above parameters are related by the simple formula: $D_O = 4 * \lambda * (EFL)/(\pi * B)$, where $D_O$ is the focused Gaussian beam diameter, $\lambda$ is the illuminating wavelength, and B is the waist diameter of the incoming collimated laser beam at the pupil. Whilst the spot size in the x direction of FIG. 2 is approximately determined from the above formula, the size of the spot in the y direction is "stretched" by a factor proportional to the inverse of the cosine of the wafer's tilt angle with respect to the pupil of the lens.

The size of the spots may also be selected such that a substantial amount of light scattered from the spots is not light scattered from a surface of the wafer. In particular, since the size of each of the spots is much smaller (e.g., about 20 times smaller) than the size of a single spot or line on a wafer plane, the spots are closer in size to the defects on the wafer than a single spot or line. In this manner, during illumination of a defect on the wafer by one of the spatially separated spots, a larger portion of the spatially separated spot will be incident on the defect than that of the single spot or line. In other words, a much smaller area of the surface of the wafer will be illuminated by each of the spatially separated spots compared to the single spot or line.

Such limited illumination of the wafer surface by each of the multiple spots necessarily causes less scattering of light from the wafer surface within each of the spots on the wafer plane. By reducing the amount of light scattered from the wafer surface, the illumination systems described herein may be used in an inspection system to increase the signal-to-noise ratio (SNR) of the inspection system. Such reduction in the scattering of light from a rough surface on a wafer is particularly important since the amount of light scattered from a rough wafer surface may be relatively high with respect to the amount of light scattered from defects on the wafer, and particularly relatively small defects. Therefore, the illumination systems described herein may be used in inspection systems not only to increase the absolute defect sensitivity of the inspection system but also to increase the sensitivity of the system for defect detection on relatively rough surfaces. As such, the inspection system embodiments described herein will have a higher SNR than a single large spot or line imaging based system by virtue of the smaller wafer area illuminated by each of the multiple spots that provides substantially enhanced rejection of background surface scattering (e.g., due to roughness).

Figure 2:
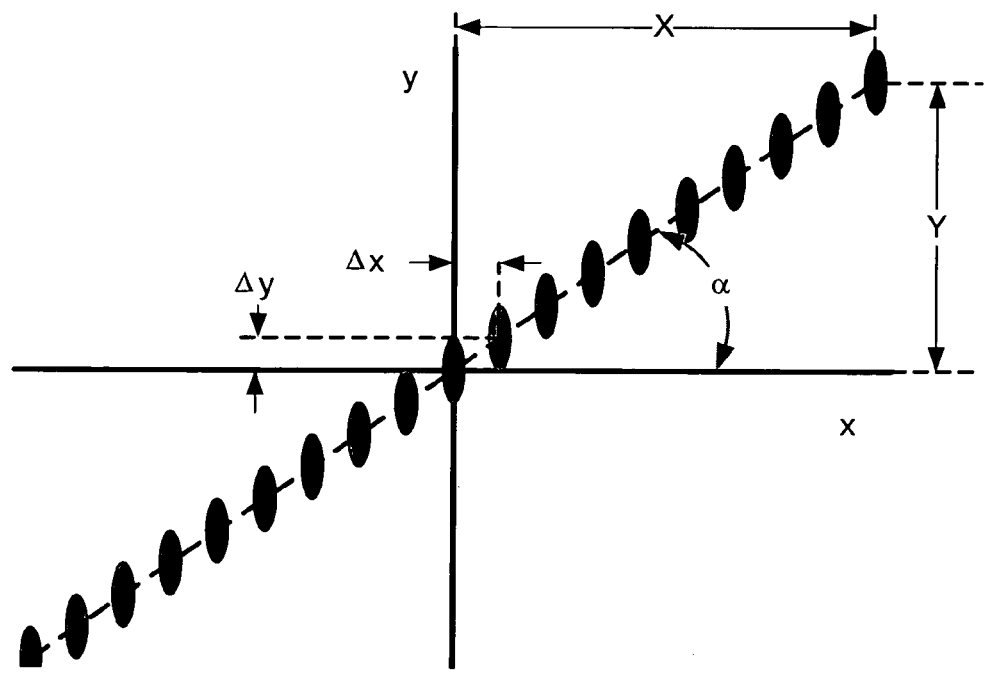
FIG. 2 is a schematic diagram illustrating a top view of one embodiment of spatially separated spots formed on a wafer plane.

As shown in FIG. 2, the spots formed on the wafer plane may be arranged along a line inclined by $\alpha$ degrees relative to the local x and y axes of the wafer plane. The angle of this line with respect to the local x and y axes may vary depending on the rotation of the illumination system with respect to the entrance pupil plane. For example, the DOE or the set of the optical elements may be rotated about a z axis of the plane of the entrance pupil. The angle of rotation of the DOE or the set of optical elements will determine the angle of the line with respect to the local x and y axes of the wafer plane. Alternatively, the angle of rotation may vary depending on the configuration of the DOE when a two-dimensional DOE is used in the system.

The x and y coordinates of the individual spots on the wafer plane are determined by the pitch of the DOE and the focal length of the illumination optics. Since it is preferable that the spots do not overlap on the wafer plane, the separation between the spots may be relatively large. In particular, the period (or pitch) of the grating can be determined from the following formula: P=wavelength/sin(diffraction angle of the first order). The separation of the spots may be defined by the distance between the centers of adjacent spots. For example, as shown in FIG. 2, the separation may be defined in the x direction as $\Delta x$, and the separation may be defined in the y direction as $\Delta y$. In one example, $\Delta x$ may be about 6.4 microns, and $\Delta y$ may be about 4.5 microns. For such separation and an illumination wavelength of 355 nm, the DOE may have a pitch of about 2.4 mm. In some applications it may be advantageous to have a greater separation between any two adjacent spots on the wafer. For example, greater separation would allow for a greater immunity to any potential cross talk that may occur at the detection plane. For example, it may be advantageous to have a separation, $\Delta x$, of 12.8 microns, and $\Delta y$ may still remain at about 4.5 microns. The DOE pitch can be chosen to satisfy any desired spot separation.

As shown in FIG. 2, the spots extend from the center spot across a lateral dimension, X, along the x axis equal to about ((the total number of spots−1)/2)×$\Delta x$. In one example, therefore, for 19 total spots and a $\Delta x$ of about 6.4 microns, X may be equal to about 57.6 microns (9×about 6.4 microns). In addition, the spots extend from the center spot across a lateral dimension, Y, along the y axis, which may be determined as described above. For example, Y may be equal to about 40.5 microns based on the examples provided above. Therefore, the spots may be located within an area of the wafer plane of about 2X times about 2Y.

The spots are formed on the wafer plane simultaneously as described herein. Therefore, during scanning of the spots over the wafer plane, each of the spots will scan across the wafer plane simultaneously. Scanning of the spots over the wafer plane may be performed in any manner known in the art (e.g., by translation and/or rotation of the wafer while the optics are stationary, by a stationary wafer position with translating or scanning optics, or a combination thereof). For the arrangement of the spot shown in FIG. 2, the spots may be scanned over the wafer plane in a direction approximately parallel to the x axis. In this manner, as the spots scan along this direction, a portion of an area on the wafer plane that was scanned by one spot will also be scanned by another "trailing" spot. As such, a portion of the wafer plane may be scanned by different spots sequentially. In other words, the scan paths of adjacent spots will partially overlap in a direction along the y axis.

As such, an entire lateral dimension of the area on the wafer plane in which the spots are located (e.g., about 2Y for scanning along the x axis) is illuminated by the spatially separated spots as the spots are scanned across the wafer plane. In this manner, although the spots themselves have relatively small sizes, the width of a swath (i.e., the width of the scan path) on the wafer may be relatively large (e.g., about 81 microns). Therefore, the throughput of an inspection system that includes an illumination system embodiment described herein may be approximately equal to or greater than the throughput of single spot or line imaging based inspection systems. Accordingly, the systems described herein provide instantaneous multi-spot scanning with the same or increased speed compared to currently used systems. In addition, although discrete, spatially separated spots are imaged on the wafer, scanning can be performed without "missing" any areas on the wafer within the scan path.

Referring back to FIG. 1, the set of optical elements may include optical element 18. Optical element 18 is a refractive optical element that is centered with respect to the x and y axes of the plane of the entrance pupil. The orientation of the x, y, and z axes of the plane of the entrance pupil are shown in FIG. 1. Optical element 18 has one spherical surface and one aspheric surface. Optical element 18 is also not tilted with respect to the entrance pupil plane. Optical element 18 may be used as a reference element. In other words, other optical elements of the set described further herein may be positioned with reference to optical element 18. Optical element 18 may also be designed such that this optical element does not substantially impact the performance of the system either negatively or positively.

In one embodiment, the set of optical elements also includes two optical elements 20 and 22 that are decentered with respect to the x and y axes of the plane of the entrance pupil. These two optical elements are also tilted with respect to the y axis. Decentering and tilting optical elements 20 and 22 as described above reduces the aberrations in the spatially separated spots formed on the wafer plane, which are described further herein. In this manner, decentering and tilting these optical components improves the performance of the illumination system and the performance of an inspection system in which the illumination system is used. In addition, as shown in FIG. 1, optical elements 20 and 22 have one spherical surface and one aspheric surface. (Although it is not shown in FIG. 1 due to the scale of the figure, optical element 20 may be a planar concave lens or a negative curvature lens.) Optical elements 20 and 22 are also refractive elements.

In another embodiment, the set of optical elements also includes a third optical element 24. The third optical element is decentered with respect the x and y axes of the plane of the entrance pupil. In addition, the third optical element is tilted with respect to the x axis of the plane of the entrance pupil. Decentering and tilting optical element 24 also reduces the aberrations in the spatially separated spots formed on the wafer plane as described further herein. As such, decentering and tilting optical component 24 also improves the performance of the illumination system and the performance of an inspection system in which the illumination system is used. As shown in FIG. 1, optical element 24 has one spherical surface and one aspheric surface. In addition, optical element 24 is a refractive optical element. Therefore, in one embodiment, all of the optical elements of the set (e.g., optical elements 18, 20, 22, and 24) are refractive optical elements. The optical elements may be formed of any suitable refractive material known in the art that has adequate transmission properties at the chosen wavelength of operation.

Figure 1A:
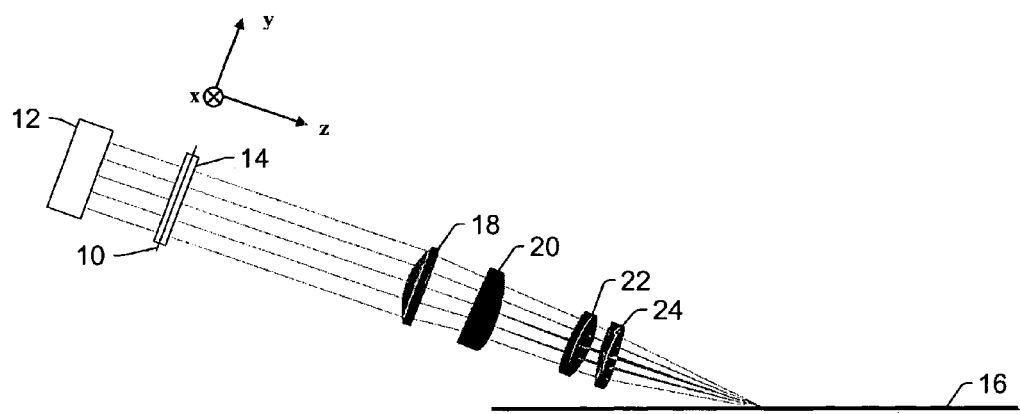
FIG. 1a is a schematic diagram illustrating a cross-sectional view of one embodiment of a system configured to provide illumination of a wafer for inspection that includes one or more truncated optical elements.

In some embodiments, the set of optical elements includes one or more truncated optical elements. For example, in one such embodiment, all of the lenses of the set, except for the first optical element (i.e., optical element 18) may be truncated in order to fit the set of optical elements into a compact mechanical housing that will provide adequate clearance between the last element (i.e., optical element 24) and the wafer plane. A clearance of a few millimeters (e.g., about 5 mm to about 6 mm) is typically adequate to facilitate easy assembly, removal, and servicing. Extending the clearance beyond that reported here results in a system that is either substantially complex and/or less well corrected thereby failing to meet the diffraction limited performance and less than perfect Gaussian shaped focused spots which are desirable for this application. Truncation of the lenses is possible due to the asymmetry of the optical system. In other words, active image forming rays do not fill the entire surface of each lens. A truncated (profiled) embodiment of the system is shown in FIG. 1a. The system shown in FIG. 1a may be configured as described further herein.

Defocus and astigmatism are typically the most important aberrations contributing to degradation of image quality in optical systems with tilted image planes. These aberrations are not a major issue if the system generates a single spot or line coincident with the tilt line (axis) as is currently performed. But when a system is configured to generate multiple spots on a wafer plane that is tilted with respect to the optical axis (e.g., as shown in FIG. 1) and with a spot distribution such as that shown in FIG. 2, the effect of these aberrations on the system performance becomes a serious issue if not corrected.

In particular, with the exception of the central spot, all other spots will be out of focus, and the focus error will increase with increasing field size (i.e., increasing number of spots) and tilt of the image plane. This defocus error also has opposite values at opposite ends of the field. In other words, the spots across the field will be in focus along a line that is perpendicular to the optical axis of the illumination system. However, this line is not parallel to the tilted wafer plane. As such, the spots at the extreme edges of the field will come into focus at different heights with respect to the wafer plane: at one edge below the wafer plane, and at the opposite edge above the wafer plane. Such defocus error is shown by way of example in FIG. 3, which includes simulated plots illustrating ray aberrations of multi-spot illumination optics that include centered spherical, aspheric, and cylindrical optical elements across the field on an inclined wafer plane. The plots were simulated for an illumination wavelength of 355 nm and an oblique angle at which the wafer plane is arranged with respect to the entrance pupil plane of 70 degrees.

Figure 3:
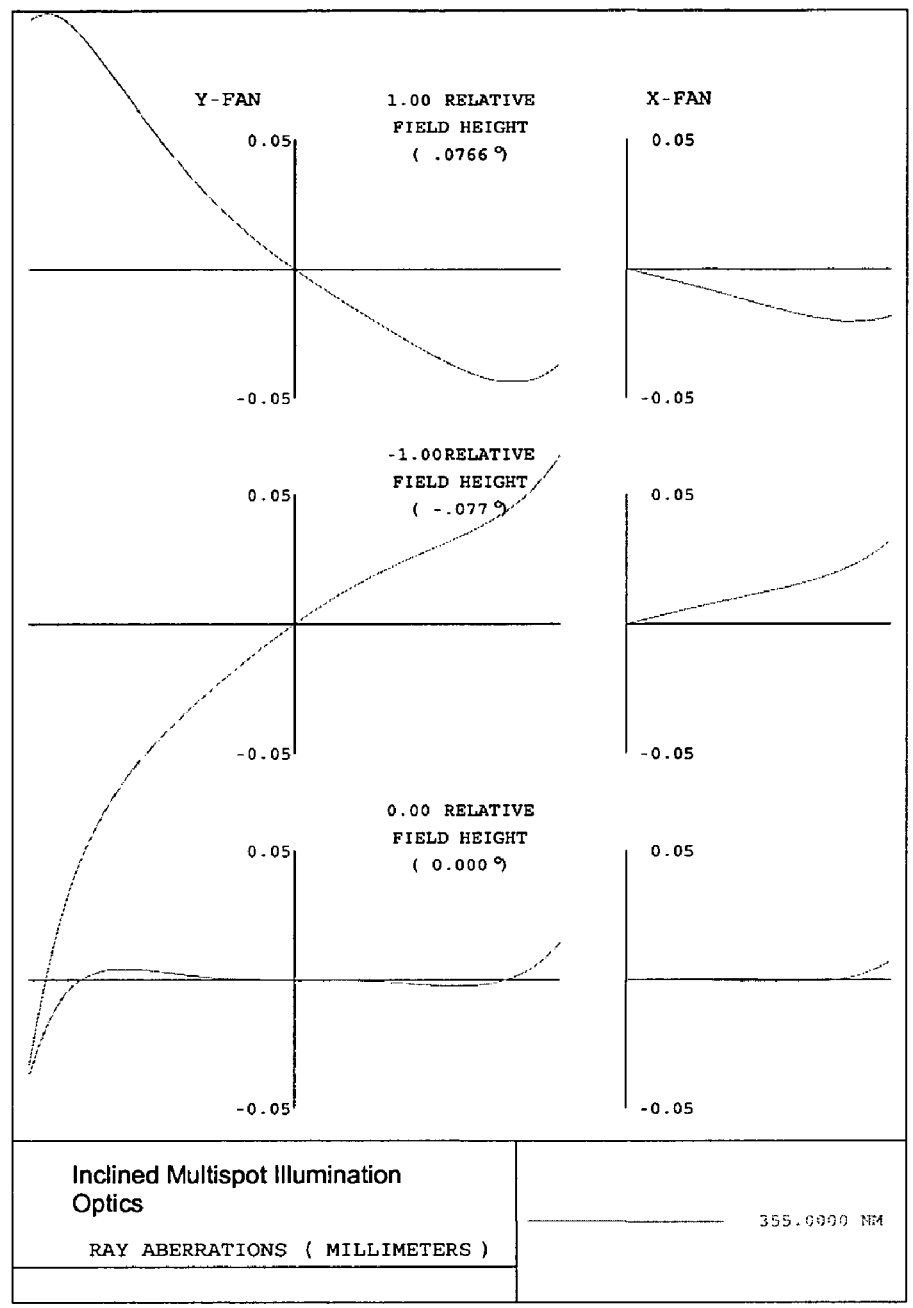
FIG. 3 includes simulated plots illustrating ray aberrations of multi-spot illumination optics that include centered spherical, aspheric, and cylindrical optical elements across the field on an inclined wafer plane.

The simulated plots on the left hand side of FIG. 3 illustrate the ray aberrations (in mm) across the field along the y axis of the pupil. The simulated plots on the right hand side of FIG. 3 illustrate the ray aberrations across one half of the field along the x axis of the pupil. From top to bottom, the plots are simulated for 1.00 relative field height, −1.00 relative field height, and 0.00 relative field height.

As shown in the plots for the positive field height along the x and y axes, the ray aberrations along the y axis change much more dramatically across the field than the ray aberrations along the x axis. Such differences in the ray aberrations along the x and y axes are also seen in the plots for negative defocus. In this manner, the focus error along the y axis will be much greater across the field than the focus error along the x axis. In addition, as shown by the ray aberrations along the y axis for the positive field height, the negative field height, and the axial field height, the ray aberrations have opposite values at opposite ends of the field. Furthermore, as shown by comparison of the ray aberrations along the x and y axes for the positive and negative field heights, as the field height switches from positive to negative, the ray aberration values at different ends of the field also switch from positive to negative or vice versa. As such, defocus of the optics in one direction will only further compromise the performance of the optics in the opposite direction. Therefore, centered optical systems incorporating spherical, aspheric, and cylindrical elements will not be able to correct for this type of asymmetric focus error.

The set of optical elements described herein is, however, configured to correct asymmetric focus error in the spots across the field in the illumination system. In particular, the embodiments of the set of optical elements described herein include aspheric optical elements, centered and decentered, some of which are tilted relative to the optical axis. In general, a minimum of two lenses, tilted in the two directions can be used. However, in embodiments described herein to keep the mechanical assembly relatively simple, three tilted/decentered elements are used: two tilted/decentered with respect to the y axis of the entrance pupil and a third tilted/decentered in a plane perpendicular to that of the other two lenses (i.e., tilted/decentered with respect to the x axis of the entrance pupil). The two optical elements that are decentered and tilted with respect to the y axis of the plane of the entrance pupil are used to correct the aberrations along the y axis, and the third optical element that is decentered and tilted with respect to the x axis is used to correct the aberrations along the x axis. Two optical elements are used to correct the aberrations along the y axis (while a single optical element can be used to correct the aberrations along the x axis) since the aberrations along the y axis are relatively severe. As such, using two optical elements for correction of the aberrations along the y axis substantially reduces the complexity of the system while achieving substantial correction of the aberrations.

All of these elements are aspheric and, except for the reference optical element, are decentered to some extent. In addition, the curvature of the lenses included in the set of optical elements (except for possibly the reference optical element) can be selected to substantially correct any astigmatism caused by the tilting and decentering of the optical elements. In this manner, the use of aspheric elements helps to compensate for the higher order aberrations introduced by the tilting/decentering of the optical elements as well as keeping the number of optical elements to the minimum possible while providing diffraction limited performance with adequate clearance between the optics and the wafer plane.

Figure 4:
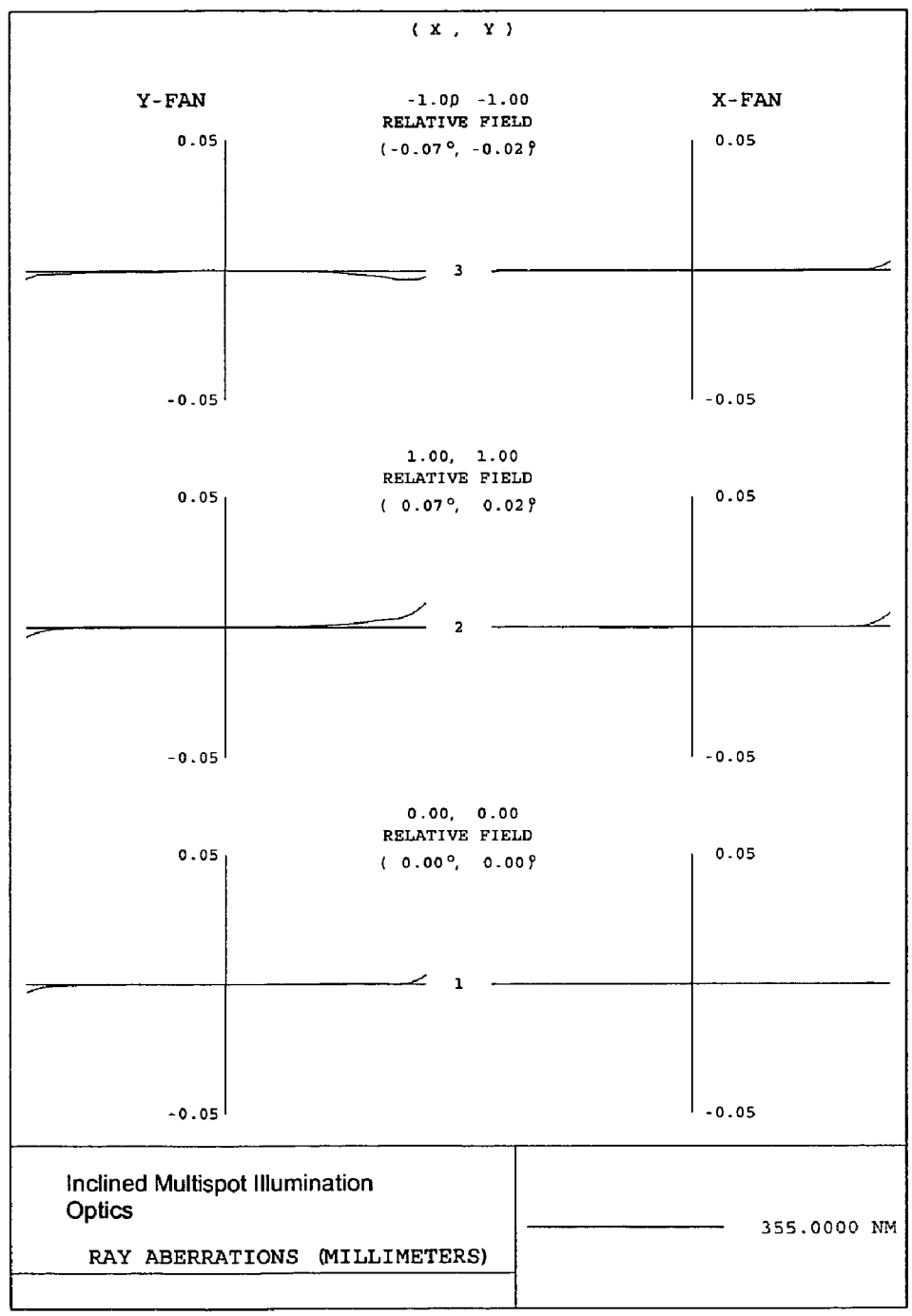
FIG. 4 includes simulated plots illustrating ray aberrations of multi-spot illumination optics configured according to embodiments described herein across the field on an inclined wafer plane.

The substantial correction of the asymmetric focus error in the spots formed on the wafer plane is illustrated by way of example in FIG. 4, which includes simulated plots illustrating ray aberrations of multi-spot illumination optics configured according to embodiments described herein across the field on an inclined wafer plane. The plots shown in FIG. 4 were simulated for an illumination wavelength of 355 nm and an oblique angle at which the wafer plane is arranged with respect to the entrance pupil plane of 70 degrees. The simulated plots on the left hand side of FIG. 4 illustrate the ray aberrations (in mm) across the field along the y axis of the pupil. The simulated plots on the right hand side of FIG. 4 illustrate the ray aberrations (in mm) across the field along the x axis of the pupil. From top to bottom, the plots are simulated for −1.00, −1.00 (x, y) relative field height, 1.00, 1.00 (x, y) relative field height, and 0.00, 0.00 (x, y) relative field height.

As shown in all of the plots for positive, negative, and axial field height along the y axis and the x axis, the ray aberrations are negligible. Therefore, the system embodiments described herein can be used to substantially correct the asymmetric focus and astigmatism errors across the field on an inclined wafer plane. In addition, by comparison of the plots shown in FIGS. 3 and 4, a set of optical elements configured according to embodiments described herein corrects even the substantial asymmetric focus errors seen in FIG. 3. Accordingly, the illumination optics described herein will have performance capabilities that are substantially better than the performance that can be achieved using centered optical systems incorporating spherical, aspheric, and cylindrical elements.

Figure 5:
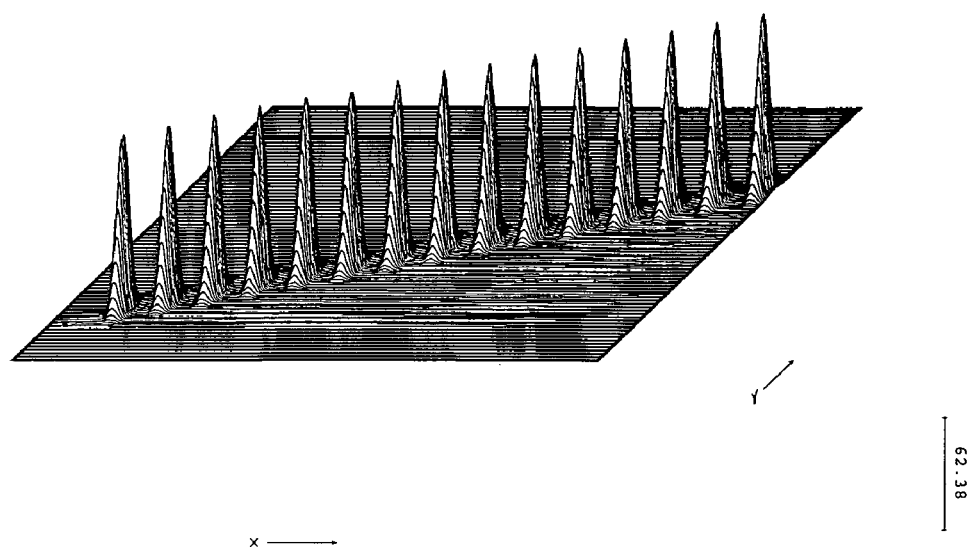
FIG. 5 is a simulated plot illustrating the point spread function (PSF) of spatially separated spots formed on a wafer plane by a system configured according to embodiments described herein.
Figure 6:
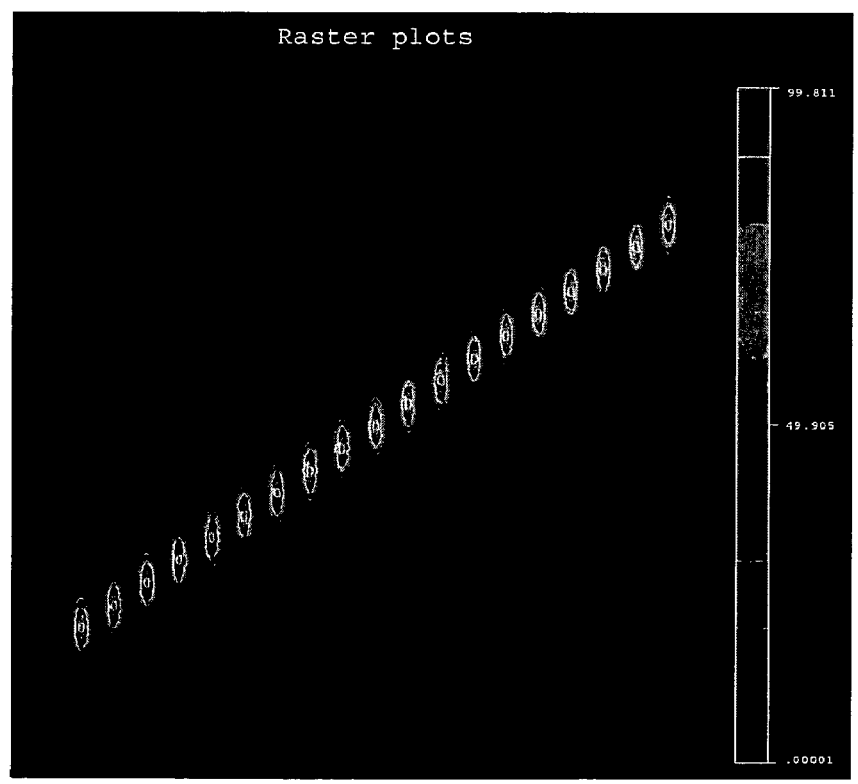
FIG. 6 is a simulated plot illustrating a raster diagram equivalent to the simulated plot of FIG. 5.

FIG. 5 is a simulated plot illustrating the point spread function (PSF) (i.e., image of a point source) for spatially separated spots formed on a tilted wafer plane by a system configured according to embodiments described herein. In particular, FIG. 5 shows the PSF of 15 out of 19 spatially separated spots that can be formed on a tilted wafer plane by the systems described herein. It is clear from this plot and the equivalent raster diagram shown in FIG. 6 that all of the spots have a perfectly formed Gaussian profile, elliptical shape, and equal intensity. This uniformity of illumination is another advantageous characteristic of the optical system configurations described herein.

It is essential for the future of unpatterned wafer inspection to devise systems with enhanced performance in terms of absolute defect sensitivity and the ability to reject background surface scattering due to roughness while maintaining current throughput levels. As described further above, the systems described herein meet both of these requirements in a design that is relatively simple, compact, and practical (at a spot size of about 3 microns×about 9 microns, each spot is about 20 times smaller than the smallest single spot presently used in the SP2 system, which is commercially available from KLA-Tencor, San Jose, Calif.).

Another embodiment relates to a method for providing illumination of a wafer for inspection. The method includes directing light to an entrance pupil. The light may be directed to the entrance pupil as described further above (e.g., using one or more optical elements such as optical element 12 shown in FIG. 1). The method also includes separating the light into individual beams at the entrance pupil. Separating the light into individual beams may be performed as described further above (e.g., using a DOE as shown in FIG. 1). The individual beams may be configured as described above (e.g., substantially collimated, etc.).

In addition, the method includes focusing the individual beams to a wafer plane to form spatially separated spots on the wafer plane. Focusing the individual beams to the wafer plane may be performed as described further above (e.g., using a set of optical elements as shown in FIG. 1). The spatially separated spots may be formed on the wafer plane as shown in FIG. 2. The spatially separated spots may be further configured as described above. For instance, the spots may be diffraction limited spots. The wafer plane is arranged at an oblique angle to the entrance pupil. The wafer plane may be arranged with respect to the entrance pupil as shown in FIG. 1. In one embodiment, focusing the individual beams to the wafer plane preferably includes correcting asymmetric focus error in the spots, which may be performed as described further above. Each of the embodiments of the method described above may be performed by any of the system embodiments described herein. In addition, each of the embodiments of the method described above may include any other step(s) described herein.

An additional embodiment relates to a system configured to inspect a wafer. The system includes one or more optical elements configured to direct light to an entrance pupil. The one or more optical elements may be configured as described above and shown in FIG. 1. In addition, the entrance pupil may be arranged as described above and shown in FIG. 1. This system also includes a DOE positioned at the entrance pupil. The DOE is configured to separate the light into individual beams. The DOE may be further configured as described above and shown in FIG. 1. In addition, the system includes a set of optical elements configured to focus the individual beams to a wafer plane to form spatially separated spots on the wafer plane. The wafer plane is arranged at an oblique angle to the entrance pupil. The wafer plane may be arranged with respect to the entrance pupil as described above and shown in FIG. 1.

The set of optical elements may be further configured as described above and shown in FIG. 1. Preferably, the set of optical elements may be configured to correct asymmetric focus error in the spots. The spots may be configured as shown in FIG. 2 and described further above. For example, the spots may be diffraction limited. In addition, a size of each of the spots may be approximately equal. The size of the spots may preferably be selected such that a substantial amount of light scattered from each of the spots is not light scattered from a rough surface of the wafer. Furthermore, the spots may be located within an area of the wafer plane such that an entire lateral dimension of the area is illuminated by the spots as the spots are scanned across the wafer plane.

The system further includes a detection subsystem that is configured to collect and detect light scattered from each of the spots. Signals generated by the detection subsystem in response to the detected light can be used to detect defects on the wafer. The detection subsystem may be further configured as described herein. The wafer may include a wafer such as an unpatterned wafer and a wafer having a relatively rough upper surface. Each of the embodiments of the inspection system described above may be further configured as described herein. For example, the inspection system may include a processor or computer system, which may be configured as described further herein. In addition, the inspection system will have all of the advantages of the illumination system described herein.

One embodiment of a system configured to collect and detect light scattered from a wafer includes a set of optical elements that is configured to collect light scattered from spatially separated spots formed on a wafer plane at an oblique angle of incidence. The wafer plane may be arranged as described further above and shown in FIG. 1. The oblique angle of incidence may be selected as described further above. The spatially separated spots may be configured as shown in FIG. 2. In addition, the spatially separated spots may be formed on the wafer plane at the oblique angle of incidence as described above (e.g., using a system configured to provide illumination of a wafer for inspection as shown in FIG. 1). The set of optical elements is also configured to focus the light to corresponding spatially separated positions in an image plane. In this manner, the set of optical elements maintains the spatial separation of the light scattered from the multiple spots from the wafer plane to the image plane.

Figure 7:
FIGS. 7 and 8 are schematic diagrams illustrating a cross-sectional view and a perspective view, respectively, of different embodiments of a set of optical elements configured to collect light scattered from spatially separated spots formed on a wafer plane at an oblique angle of incidence and to focus the light to corresponding spatially separated positions in an image plane.

One embodiment of a set of optical elements that is configured as described above is shown in FIG. 7. As shown in FIG. 7, the set of optical elements includes optical elements 26, 28, and 30. Optical element 26 is configured to collect light scattered from spatially separated spots (not shown in FIG. 7) formed on wafer plane 32 at an oblique angle of incidence. Optical element 28 is configured to direct the light collected by optical element 26 to optical element 30. Optical element 30 is configured to focus the light to spatially separated positions (not shown in FIG. 7) in image plane 34.

Optical elements 26, 28, and 30 include spherical/aspheric optical elements. In other words, each of the optical elements may have one spherical surface and one aspheric surface. The spherical/aspheric optical elements are configured as lenses or refractive optical elements. The lenses may be formed of any suitable refractive material known in the art that has adequate transmission properties at the chosen wavelength of operation. For simple construction of the systems described herein, the refractive index of optical element 26 may be rather high since more complex and/or less well corrected construction may result from a lower refractive index of optical element 26. A field size of the set of optical elements is preferably equal to or larger than an area in which the spots formed on the wafer plane are located. For instance, the field size of the set of optical elements may be about 140 microns in diameter for the above-described 19 illuminated spots on the wafer plane. The set of optical elements is preferably configured to generate highly corrected images at the spatially separated positions in the image plane.

A numerical aperture (NA) of the set of optical elements may be relatively high. For example, in one embodiment, the NA of the set of optical elements is equal to 0.94. In this manner, the NA of the set of optical elements enables an inspection system in which the collection and detection system is used to have relatively high sensitivity. In particular, the sensitivity of a system that includes the set of optical elements configured as described herein may be higher than the sensitivity of systems configured for collection and detection of light scattered from a single large spot or line on the wafer plane at an oblique or normal angle of incidence or multiple spots on the wafer plane at a normal angle of incidence.

As shown in FIG. 7, the set of optical elements may be positioned relatively close to wafer plane 32. Such proximity between the set of optical elements and the wafer plane is preferable due to the large NA of the optical elements. For example, due to the large NA, the diameter and thickness of the optical elements tend to grow rapidly unless the optical elements are brought substantially close to the wafer plane. Therefore, in system embodiments described herein, the distance between the wafer plane and the first optical element (e.g., optical element 26) may be kept at a minimum to provide adequate clearance, yet permit manageable lens sizes to be used in the system. Such proximity between the set of optical elements and the wafer plane produces an immediate conflict with the illumination optics described further above and shown in FIG. 1. In particular, the illumination optics are also located relatively close to the wafer plane.

Figure 8:
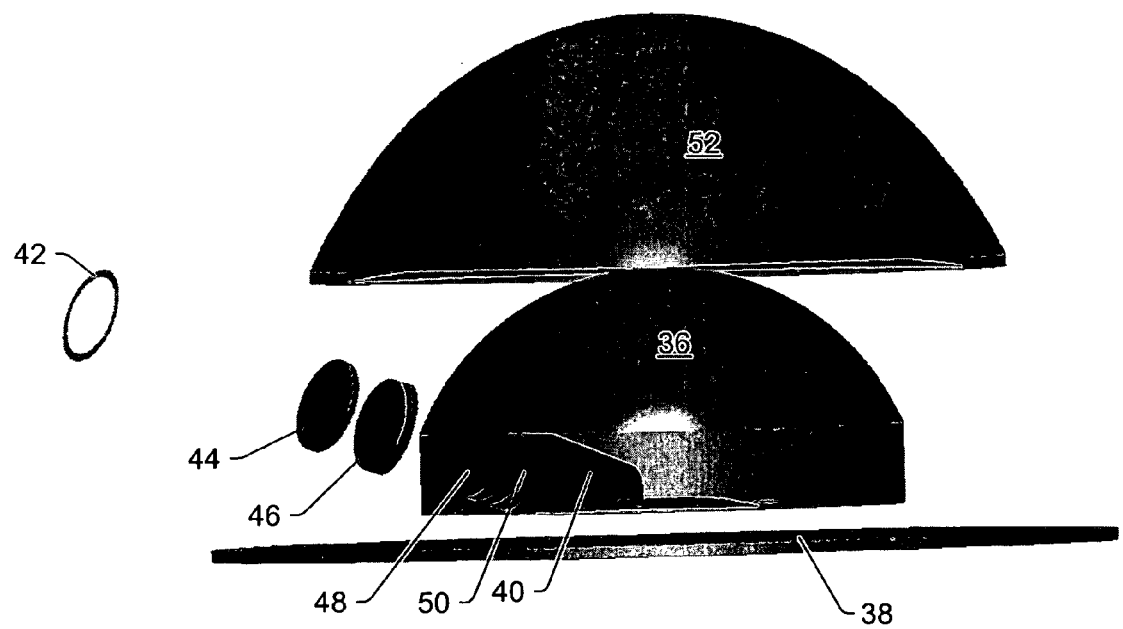

FIG. 8 illustrates another embodiment of the set of optical elements that provides a solution to overcome this problem. In particular, as shown in FIG. 8, the set of optical elements includes first optical element 36, which is located closest to wafer plane 38 and is configured to collect light scattered from the wafer plane. As further shown in FIG. 8, section 40 of the first optical element is removed such that light can be directed through section 40 to wafer plane 38 at the oblique angle of incidence. Section 40 may have a cylindrical or conical shape. In addition, section 40 may extend through the first optical element such that the light used for illumination does not interact with the first optical element. In this manner, the illumination may travel through free space within the removed section and one or more optical elements of the illumination subsystem that can be positioned within the removed section.

In particular, the illumination subsystem shown in FIG. 8 includes a set of optical elements that is configured to focus individual beams of light on wafer plane 38. Wafer plane 38 is arranged at an oblique angle to entrance pupil 42. A DOE (not shown in FIG. 8), which may be configured as described above, is positioned at the entrance pupil and is configured to separate the light into the individual beams. The set of optical elements includes optical elements 44, 46, 48, and 50, each of which may be configured as described above. For example, optical element 44 may be configured for use as a reference optical element. Optical elements 46 and 48 may be decentered and tilted with respect to the entrance pupil to correct asymmetric focus error in the spots formed on the wafer plane in a direction along a y axis of a plane of the entrance pupil. Optical element 50 may be decentered and tilted with respect to the entrance pupil to correct asymmetric focus error in the spots formed on the wafer plane in a direction along a x axis of the plane of the entrance pupil.

As further shown in FIG. 8, optical elements 48 and 50 are positioned in the removed section of first optical element 36. In this manner, the illumination optics are actually positioned within the collection optics. As such, the illumination optics are configured to direct light through section 40 to wafer plane 38. In this manner, the configuration of the collection optics allows compact integration with the above described tilted multi-spot illumination system.

The configuration of first optical element 36 shown in FIG. 8 results in some of the scattered light from the wafer plane being blocked mainly by the illumination optics and to a smaller extent by the removed section of the first optical element. However, by judicious profiling of the elements of the illumination optics and the cylindrical/conical removed section of the first optical element of the collection system, the obscuration of the scattered light may be kept to a minimum. For instance, the elements of the illumination subsystem may be designed to be as small as possible without compromising the performance of the illumination subsystem.

The system shown in FIG. 8 may be further configured as described herein. For instance, the collection and detection optics include optical element 52, which like optical element 28 described above, may be configured to direct the collected light to another optical element (not shown due to the scale of FIG. 8). This other optical element may be configured to focus the light to an image plane (not shown in FIG. 8) as described above. Therefore, this optical element may be configured as optical element 30 described above.

Figure 9:
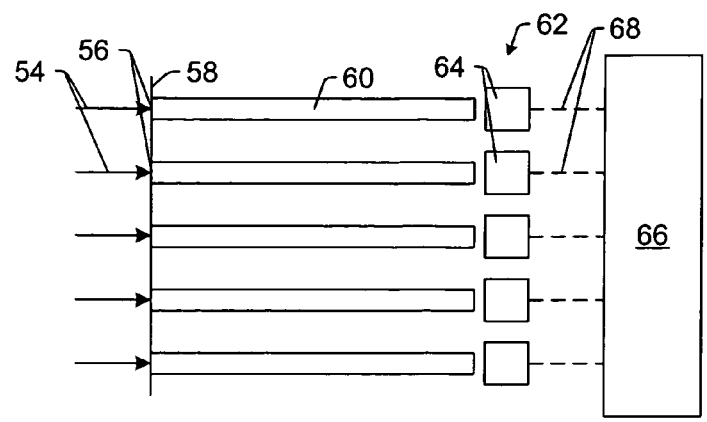
FIG. 9 is a schematic diagram illustrating a cross-sectional view of one embodiment of a detection subsystem and one embodiment of a set of optical fibers.

The system configured to collect and detect light scattered from a wafer also includes a detection subsystem that is configured to separately detect the light focused to the spatially separated positions in the image plane. One embodiment of a detection subsystem that can be used in the systems described herein is shown in FIG. 9. As shown in FIG. 9, light 54 scattered from spatially separated spots formed on a wafer plane (not shown in FIG. 9), which was collected by the set of optical elements described above, is focused to corresponding spatially separated positions 56 in image plane 58. Although only 5 spatially separated positions in the image plane are shown in FIG. 9, it is to be understood that the number of positions in the image plane to which light is focused will be equal to the number of spatially separated spots formed on the wafer plane (e.g., 19 spots and 19 spatially separated positions).

As further shown in FIG. 9, in one embodiment, the system may include a set of optical fibers 60. The set of optical fibers is configured to separately transmit the light from the spatially separated positions in the image plane to detection subsystem 62. In other words, individual optical fibers of the set are positioned such that each optical fiber receives light from one spatially separated position in the image plane. In this manner, each optical fiber preferably receives light from only one corresponding position in the image plane. Although only 5 optical fibers are shown in FIG. 9, the number of optical fibers included in the set is preferably equal to the number of spatially separated positions in the image plane to which light is focused.

As further shown in FIG. 9, the set of optical fibers may include a linear array of optical fibers. The linear array of optical fibers is preferably arranged at an angle of rotation with respect to the image plane such that the positions of the optical fibers correspond to the spatially separated positions in the image plane. In other words, the linear array of optical fibers is preferably arranged substantially parallel to the line along which the spatially separated positions are arranged in the image plane.

In one embodiment, the diameter of each of the optical fibers may be about 250 microns. The diameter of the optical fibers may be selected based on, for example, the size of the spots formed on the wafer plane, the magnification ratio of the collecting and focusing optics, and a selected magnification ratio for the system. In some embodiments, the magnification ratio of the system is greater than about 30×. In one such embodiment, based on the spot sizes described above, an optical fiber diameter of about 250 microns produces a magnification ratio of about 32×. The optical fibers may include any suitable optical fibers known in the art that have the selected diameter. Optical fibers having many different diameters are commercially available from various sources known in the art.

As further shown in FIG. 9, in one embodiment, detection subsystem 62 includes individual detectors 64 having positions that correspond to the spatially separated positions in the image plane. In other words, each of the individual detectors is configured to detect light from one position in the image plane. In this manner, each detector preferably detects light from only one position in the wafer plane. Therefore, although only 5 individual detectors are shown in FIG. 9, the number of individual detectors included in the detection subsystem is preferably equal to the number of spatially separated positions in the image plane to which light is focused. As shown in FIG. 9, when the system includes a set of optical fibers, each detector may actually detect the light transmitted by only one optical fiber of the set.

In addition, although the spacing between the optical fibers is shown in FIG. 9 to be relatively constant along the length of the optical fibers, it is to be understood that the spacing between the optical fibers may be different at the image plane and at the detection subsystem based on, for example, the separation between the positions in the wafer plane and the size of the individual detectors of the detection subsystem. Furthermore, although the individual detectors are shown in FIG. 9 arranged in a linear array corresponding to the linear array of the spatially separated positions in the image plane, it is to be understood that the individual detectors may be arranged in any manner (e.g., a two dimensional array) as long as the set of optical fibers can be arranged to direct light to the individual detectors. In this manner, the arrangement of the individual detectors does not have to reflect that of the spatially separated positions in the image plane and can be selected to improve the compactness of the system.

Each detector is configured to generate signals responsive to the light detected by the detector. In this manner, the detection subsystem is configured to generate different signals for the light focused to different positions in the image plane. As such, a different signal can be generated independently for the light scattered from each individual spot on the wafer plane. The signals generated by each detector may be responsive to, for example, an intensity of the light scattered from each of the spots formed on the wafer plane. However, the signals may be responsive to any measurable property of the light scattered from each of the spots formed on the wafer plane. Each of the individual detectors may be, for example, a charge coupled device (CCD) or any other suitable detector known in the art.

In an alternative embodiment, the system may not include the set of optical fibers. In such an embodiment, the detection subsystem may be configured to detect the light at the spatially separated positions in the image plane. For example, the individual detectors of the detection subsystem may be arranged such that the photosensitive areas of the detectors are located at the image plane.

In an additional embodiment, the detection subsystem may include multiple detectors as described above or a single detector that can separately detect the light focused to spatially separated positions in the image plane. For example, such a detector includes a multi-anode photomultiplier tube (PMT) or any other segmented detector known in the art. In this manner, the single detector preferably generates different signals for the light focused to each of the spatially separated positions in the image plane. Such a single segmented detector may also be used in the detection subsystem for system embodiments that include the set of optical fibers described above. In such embodiments, the individual photosensitive areas of the detector may be positioned as described above with respect to the set of optical fibers.

As shown in FIG. 9, each of the individual detectors may be coupled to processor 66 by transmission medium 68. The transmission media may include any suitable transmission media known in the art. In addition, one or more additional components (not shown) may be interposed between the detectors and the processor such as analog-to-digital converters. Processor 66 may be configured to separately process signals from different detectors. For instance, processor 66 may be configured to determine if signals from different detectors include defect signals. In this manner, the processor may be configured to separately analyze the light scattering signals for each spot on the wafer plane. The processor may be configured to detect defects on the wafer using any method or algorithm known in the art. The processor may also be configured to perform other defect-related functions such as defect classification. The processor may include any appropriate processor or computer system known in the art. For example, the processor may be configured to have parallel processing capability.

Figure 10:
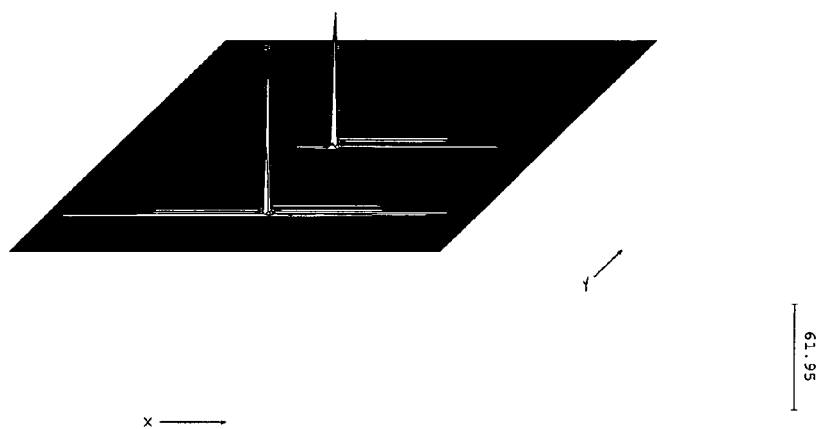
FIGS. 10 and 11 are simulated plots illustrating the energy distribution of light focused to two adjacent spatially separated positions in an image plane with in-focus and out-of-focus conditions, respectively.
Figure 11:
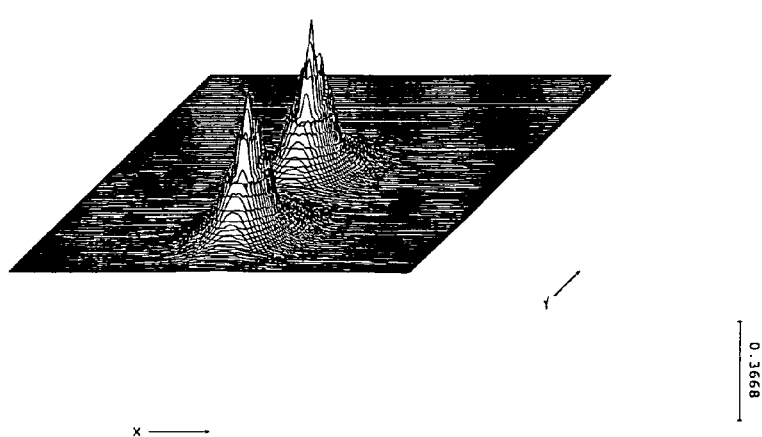

In one embodiment, the sets of optical elements shown in FIGS. 7 and 8 are overcorrected, or at least well corrected, to reduce degradation in imaging quality at the image plane due to focus error. For example, FIG. 10 illustrates the energy distribution at the input face of two adjacent detectors (or fibers). The energy distributions are shown for one position located at one end of the image plane and the position located adjacent to it. As shown in FIG. 10, the two images are well separated with no leakage of energy from one position to the other. This situation changes dramatically with a slight focus error in the plane of the wafer. This situation is shown in FIG. 11, where a 2 micron defocus of the wafer plane has caused a significant spread of the light in each position. Therefore, in the absence of focus compensation and with a relatively large NA, the system is preferably well corrected to counteract the significant degradation of the image quality due to even relatively small amounts of focus error. For example, the system is diffraction limited as described further above. Therefore, the system is well corrected. In addition, as described further above, the aberrations in the system are negligible. The system may also have a Strehl ratio of about 90% or greater.

A system configured to collect and detect light scattered from a wafer as described above, therefore, can be used with an illumination system configured according to embodiments described herein for a multi-spot obliquely illuminated wafer plane. The system also advantageously includes all-refractive relatively simple imaging optics for use with the highly inclined wafer illumination optics. In addition, the collection and detection system provides a substantially high NA (e.g., equal to 0.94) system with relatively high sensitivity to both un-patterned and rough wafer surfaces. Furthermore, neither single spot or line illumination based collection systems nor normally illuminated multi-spot based collection systems are suitable as collectors for use with the highly inclined multi-spot illumination optics described herein. Therefore, the collection and detection systems described herein provide a solution for such illumination systems for which no other solution is currently available. As such, the collection and detection systems described herein will have the same advantages as those of the illumination systems described further above.

The systems described herein for collection and detection of light scattered from a wafer may be included in an inspection system. For example, in one embodiment, a system configured to inspect a wafer includes an illumination subsystem that is configured to direct light to a wafer plane at an oblique angle of incidence to form spatially separated spots on the wafer plane. The illumination subsystem may be further configured according to the embodiments described herein and shown in FIG. 1.

The inspection system also includes a set of optical elements configured to collect light scattered from the spots and to focus the collected light to corresponding spatially separated positions in an image plane. The set of optical elements may be configured according to embodiments described herein and shown in FIGS. 7 and 8. For example, an NA of the set of optical elements may be equal to 0.94. In addition, a field size of the set of optical elements may be equal to or larger than an area in which the spots on the wafer plane are located. Furthermore, the set of optical elements may include a first optical element, and a section of the first optical element may be removed. In such an embodiment, the illumination subsystem may be configured to direct the light through the section to the wafer plane. Moreover, the set of optical elements may be overcorrected to reduce degradation in imaging quality at the image plane due to focus error.

The inspection system further includes a detection subsystem configured to separately detect the light focused to the spatially separated positions in the image plane. In one embodiment, the system includes a set of optical fibers configured to separately transmit the light from the spatially separated positions in the image plane to the detection subsystem. The detection subsystem and the set of optical fibers may be configured according to embodiments described herein and shown in FIG. 9. For example, the detection subsystem may include individual detectors having positions that correspond to the spatially separated positions in the image plane. As described above, signals generated by the detection subsystem in response to the detected light can be used to detect defects on the wafer. The wafer may include wafers such as an unpatterned wafer and a wafer having a relatively rough surface. The inspection system may be further configured as described herein. In addition, the inspection system will have all of the advantages of the illumination system and the collection and detection system described herein.

An additional embodiment relates to a method for collecting and detecting light scattered from a wafer. The method includes collecting light scattered from spatially separated spots formed on a wafer plane at an oblique angle of incidence. Collecting the light scattered from the spatially separated spots may be performed as described above and shown in FIGS. 7 and 8. The spatially separated spots may be formed on the wafer plane using an illumination system configured as described above and shown in FIG. 1. The spatially separated spots may be formed on the wafer plane as shown in FIG. 2.

The method also includes focusing the light to corresponding spatially separated positions in an image plane. Focusing the light may be performed as described above and shown in FIGS. 7 and 8. In addition, the method includes separately detecting the light focused to the spatially separated positions in the image plane. Separately detecting the light may be performed as described herein and shown in FIG. 9.

The method may include any other step(s) described herein. For example, the method may include directing light through a removed section of an optical element, used for collecting the scattered light, to the wafer plane at the oblique angle of incidence to form the spatially separated spots on the wafer plane. The light may be directed in such a manner as described herein and shown in FIG. 8. In another example, the method may include separately transmitting the light from the spatially separated positions in the image plane to the detection subsystem. Separately transmitting the light from the spatially separated positions may be performed as described herein and shown in FIG. 9. In addition, the method may be performed by any of the system embodiments described herein.

In some embodiments, the systems described herein may be configured as a "stand alone tool" or a tool that is not physically coupled to a process tool. However, such a system may be coupled to the process tool by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a "cluster tool" or a number of process modules coupled by a common handler.

The results of inspection performed by the systems described herein may be used to alter a parameter of a process or a process tool using a feedback control technique, a feedforward control technique, or an in situ control technique. The parameter of the process or the process tool may be altered manually or automatically.

Further modifications and alternative embodiments of various aspects of the invention may be apparent to those skilled in the art in view of this description. For example, multi-spot illumination and collection optics for highly tilted wafer planes are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to provide illumination of a wafer for inspection, comprising:
   one or more optical elements configured to direct light to an entrance pupil;
   a diffractive optical element positioned at the entrance pupil and configured to separate the light into individual beams; and
   a set of optical elements configured to focus the individual beams to a wafer plane to form spatially separated spots on the wafer plane, wherein the wafer plane is arranged at an oblique angle to the entrance pupil, wherein the set of optical elements comprises two optical elements, wherein the two optical elements are decentered with respect to x and y axes of a plane of the entrance pupil, and wherein the two optical elements are tilted with respect to the y axis.

2. The system of claim 1, wherein the spots are diffraction limited.

3. The system of claim 1, wherein each of the spots has a Gaussian profile.

4. The system of claim 1, wherein each of the individual beams is substantially collimated.

5. The system of claim 1, wherein the intensity of each of the spots is approximately equal.

6. The system of claim 1, wherein a size of each of the spots is approximately equal, and wherein the size is selected such that a substantial amount of light scattered from the spots is not light scattered from a rough surface of the wafer.

7. The system of claim 1, wherein the oblique angle is about 70 degrees.

8. The system of claim 1, wherein the spots are located within an area of the wafer plane such that an entire lateral dimension of the area is illuminated by the spots as the spots are scanned across the wafer plane.

9. The system of claim 1, wherein the set of optical elements further comprises a third optical element, wherein the third optical element is decentered with respect to the x and y axes of the plane of the entrance pupil, and wherein the third optical element is tilted with respect to the x axis.

10. The system of claim 1, wherein the set of optical elements is further configured to correct asymmetric focus error in the spots.

11. The system of claim 1, wherein the set of optical elements further comprises refractive optical elements.

12. The system of claim 1, wherein the set of optical elements further comprises one or more truncated optical elements.

13. The system of claim 1, wherein the diffractive optical element or the set of optical elements is rotated about a z axis of the plane of the entrance pupil.

14. A system configured to inspect a wafer, comprising:
   one or more optical elements configured to direct light to an entrance pupil;
   a diffractive optical element positioned at the entrance pupil and configured to separate the light into individual beams;
   a set of optical elements configured to focus the individual beams to a wafer plane to form spatially separated spots on the wafer plane, wherein the wafer plane is arranged at an oblique angle to the entrance pupil, wherein the set of optical elements comprises two optical elements, wherein the two optical elements are decentered with respect to x and y axes of a plane of the entrance pupil, and wherein the two optical elements are tilted with respect to the y axis; and
   a detection subsystem configured to collect and detect light scattered from each of the spots, wherein signals generated by the detection subsystem in response to the detected light can be used to detect defects on the wafer.

15. The system of claim 14, wherein the spots are diffraction limited.

16. The system of claim 14, wherein a size of each of the spots is approximately equal, and wherein the size is selected such that a substantial amount of the light scattered from each of the spots is not light scattered from a rough surface of the wafer.

17. The system of claim 14, wherein the set of optical elements is further configured to correct asymmetric focus error in the spots.

18. The system of claim 14, wherein the spots are located within an area of the wafer plane such that an entire lateral dimension of the area is illuminated by the spots as the spots are scanned across the wafer plane.

19. A method for providing illumination of a wafer for inspection, comprising:

directing light to an entrance pupil;

separating the light into individual beams at the entrance pupil; and focusing the individual beams to a wafer plane using a set of optical elements to form spatially separated spots on the wafer plane, wherein the wafer plane is arranged at an oblique angle to the entrance pupil, wherein the set of optical elements comprises two optical elements, wherein the two optical elements are decentered with respect to x and y axes of a plane of the entrance pupil, and wherein the two optical elements are tilted with respect to the y axis.

* * * * *